US011655503B2

(12) United States Patent
Thompson

(10) Patent No.: US 11,655,503 B2
(45) Date of Patent: May 23, 2023

(54) SELECTIVE CAPTURE OF TARGET DNA SEQUENCES

(71) Applicant: PERSONAL GENOME DIAGNOSTICS INC., Baltimore, MD (US)

(72) Inventor: John F. Thompson, Warwick, RI (US)

(73) Assignee: Personal Genome Diagnostics Inc., Baltimore, MD (US)

( * ) Notice: Subject to any disclaimer, the term of this patent is extended or adjusted under 35 U.S.C. 154(b) by 0 days.

(21) Appl. No.: 17/316,566

(22) Filed: May 10, 2021

(65) Prior Publication Data

US 2021/0348225 A1 Nov. 11, 2021

Related U.S. Application Data

(60) Provisional application No. 63/022,968, filed on May 11, 2020.

(51) Int. Cl.
*C12Q 1/68* (2018.01)
*C12Q 1/6869* (2018.01)
*C12Q 1/6818* (2018.01)

(52) U.S. Cl.
CPC ......... *C12Q 1/6869* (2013.01); *C12Q 1/6818* (2013.01)

(58) Field of Classification Search
CPC ............................ C12Q 1/6869; C12Q 1/6818
See application file for complete search history.

(56) References Cited

U.S. PATENT DOCUMENTS

| 2011/0171644 | A1 | 7/2011 | Luo et al. | |
| 2017/0101676 | A1* | 4/2017 | Teng | C12Q 1/6869 |
| 2018/0142289 | A1 | 5/2018 | Zeutoun et al. | |

OTHER PUBLICATIONS

Andermann et al., "Guide to Carrying Out a Phylogenomic Target Sequence Capture Project", Front Genet., 2019, 10(1407):1-20.
Dapprich et al., "The next generation of target capture technologies—large DNA fragment enrichment and sequencing determines regional genomic variation of high complexity", BMC Genomics, 2016, 17(486):1-14.
Lee et al., "Improving the efficiency of genomic loci capture using oligonucleotide arrays for high throughout resequencing", BMC Genomics, 2009, 10(646):1-12.
PCT International Search Report and Written Opinion in International Application No. PCT/US2021/031623, dated Sep. 24, 2021, 17 pages.
Shih et al., "Application of Probe Capture Enrichment Next Generation Sequencing for Whole Mitochondrial Genome and 426 Nuclear SNPs for Forensically Challenging Samples", Genes, 2018, 9(1):49, 19 pages.
Zhang et al., "dCATCH-Seq: improved sequencing of large continuous genomic targets with double hybridization", BMC Genomics, 2017, 18(811):1-10.

* cited by examiner

*Primary Examiner* — Jezia Riley
(74) *Attorney, Agent, or Firm* — Kilpatrick Townsend & Stockton LLP

(57) ABSTRACT

Many regions of genomic DNA are highly similar to other regions of the genome and thus are very difficult to capture without also capturing the similar, undesired regions. This leads to over-sequencing of regions for which there is no interest and lowers coverage of the desired regions. To minimize the capture of non-desired regions, blocking baits have been designed to prevent similar but non-desired fragments from being captured. This allows more directed sequencing of the regions of interest. Blocking baits differ from capture baits in that they have modestly different sequence that preferentially bind the non-desired DNA and do not contain a biotin or other modification so remain behind when the capture baits are selected.

20 Claims, No Drawings
Specification includes a Sequence Listing.

SELECTIVE CAPTURE OF TARGET DNA SEQUENCES

CROSS-REFERENCE TO RELATED APPLICATIONS

This application claims benefit of priority under 35 U.S.C. § 119(e) of U.S. Ser. No. 63/022,968, filed May 11, 2020, the entire contents of which is incorporated herein by reference in its entirety.

INCORPORATION OF SEQUENCE LISTING

The material in the accompanying sequence listing is hereby incorporated by reference into this application. The accompanying sequence listing text file, name PGDX3140-1_SL.txt, was created on May 5, 2021, and is 8 kb. The file can be accessed using Microsoft Word on a computer that uses Windows OS.

BACKGROUND OF THE INVENTION

Field of the Invention

The present invention relates generally to sequencing highly repetitive regions of the genome and more specifically to the use of capture nucleic acid molecules and blocking nucleic acid molecules to sequence regions of the genome with repetitive DNA sequences.

Background Information

Current hybridization capture baits work effectively with unique sequences and allow the capture and deep sequencing of regions of the genome thought to be involved in cancer and other diseases. When the sequence being captured is not unique but highly similar to other sequences, there is an unavoidable capture of many thousands of regions from throughout the genome that are not desired but end up being sequenced anyway. Presently, this leads to many sequence reads that cannot be mapped or aligned properly and need to be discarded. This represents wasted sequence capacity that could be used elsewhere. Even worse, some of these sequences may be misaligned and cause false positives in the regions of interest. This is particularly problematic in intronic regions that are often needed for localizing translocations.

SUMMARY OF THE INVENTION

The present invention is based on the seminal discovery that the use of capture nucleic acid molecules and blocking nucleic acid molecules increases the accuracy of sequencing highly repetitive and/or related regions of the genome.

In one embodiment, the present invention provides methods of sequencing a target sequence by hybridizing a sample nucleic acid with a capture nucleic acid molecule and a blocking nucleic acid molecule, wherein the sample nucleic acid has the target sequence and non-target sequence; isolating the capture nucleic acid molecule hybridized to the target sequence; and sequencing the isolated target sequence.

In one aspect, the non-target sequence has a repetitive and/or related region of nucleic acid. In another aspect, the blocking nucleic acid molecule and the capture nucleic acid molecule have at least about 60 to at least about 120 nucleic acids. In an additional aspect, the capture nucleic acid is labeled with a detectable label, including but not limited to radioactive phosphates, biotin, fluorophores, enzymes or combinations thereof. In a further aspect, the blocking nucleic acid molecule is present in about 10× fold excess of the capture nucleic acid molecule. In one aspect, the blocking nucleic acid molecule has at least about 70% sequence identity to the capture nucleic acid molecule. In another aspect, the blocking nucleic acid molecule has at least about four nucleic acid molecules different from the capture nucleic acid molecule. In an additional aspect, the target sequence has at least about 60 to at least about 120 nucleic acids. In a further aspect, the sequencing is by next generation sequencing.

In another embodiment, the present invention provides methods of improving sequencing specificity and/or accuracy of a target sequence by hybridizing a sample nucleic acid with a capture nucleic acid molecule and a blocking nucleic acid molecule, wherein the sample nucleic acid has the target sequence and non-target sequence; isolating the capture nucleic acid molecule hybridized to the target sequence; and sequencing the target sequence.

In one aspect, the non-target sequence has a repetitive and/or related region of nucleic acid. In another aspect, the blocking nucleic acid molecule and the capture nucleic acid molecule have at least about 60 to at least about 120 nucleic acids. In an additional aspect, the capture nucleic acid is labeled with a detectable label, including but not limited to radioactive phosphates, biotin, fluorophores, enzymes or combinations thereof. In a further aspect, the blocking nucleic acid molecule is present in about 10× fold excess of the capture nucleic acid molecule. In one aspect, the blocking nucleic acid molecule has at least about 70% sequence identity to the capture nucleic acid molecule. In another aspect, the blocking nucleic acid molecule has at least about four nucleic acid molecules different from the capture nucleic acid molecule. In an additional aspect, the target sequence has at least about 60 to at least about 120 nucleic acids. In a further aspect, the sequencing is by next generation sequencing.

DETAILED DESCRIPTION OF THE INVENTION

The present invention is based on the seminal discovery that the use of capture nucleic acid molecules and blocking nucleic acid molecules increases the accuracy of sequencing highly repetitive and/or related regions of the genome.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, it will be understood that modifications and variations are encompassed within the spirit and scope of the instant disclosure. The preferred methods and materials are now described.

The present invention provides a method for adding blocking baits to the hybridization capture that are designed to preferentially bind to unwanted regions and prevent their capture. Without the interfering homologous repeat sequences, the desired regions can then be selectively captured for sequencing. In addition to the modest difference in sequence between the targeting baits and the blocking baits, the blocking baits do not contain biotin or other tags required for capture. The blocking baits interfere with the capture of undesired sequences but have minimal impact on the capture of the desired regions.

Many regions of genomic DNA are highly similar to other regions of the genome and thus are very difficult to capture without also capturing the similar, undesired regions. This leads to over-sequencing of regions for which there is no interest and lowers coverage of the desired regions. To minimize the capture of non-desired regions, blocking baits have been designed to prevent similar but non-desired fragments from being captured. This allows more directed sequencing of the regions of interest. Blocking baits differ from capture baits in that they have modestly different sequence that preferentially bind the non-desired DNA and do not contain a biotin or other modification so remain behind when the capture baits are selected.

In one embodiment, the present invention provides methods of sequencing a target sequence by hybridizing a sample nucleic acid with a capture nucleic acid molecule and a blocking nucleic acid molecule, wherein the sample nucleic acid has the target sequence and non-target sequence; isolating the capture nucleic acid molecule hybridized to the target sequence; and sequencing the isolated target sequence. In one aspect, the non-target sequence has a repetitive and/or related region of nucleic acid. In another aspect, the blocking nucleic acid molecule and the capture nucleic acid molecule have at least about 60 to at least about 120 nucleic acids. In an additional aspect, the capture nucleic acid is labeled with a label including but not limited to radioactive phosphates, biotin, fluorophores, enzymes or combinations thereof. In a further aspect, the blocking nucleic acid molecule is present in about 10× fold excess of the capture nucleic acid molecule. In one aspect, the blocking nucleic acid molecule has at least about 70% sequence identity to the capture nucleic acid molecule. In another aspect, the blocking nucleic acid molecule has at least about four nucleic acid molecules different from the capture nucleic acid molecule. In an additional aspect, the target sequence has at least about 60 to at least about 120 nucleic acids. In a further aspect, the sequencing is by next generation sequencing.

The phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded and may represent a sense or antisense strand, to peptide nucleic acid (PNA), or to any DNA-like or RNA-like material, natural or synthetic in origin. The phrases "nucleic acid" or "nucleic acid sequence" includes oligonucleotide, nucleotide, polynucleotide, or to a fragment of any of these, to DNA or RNA (e.g., mRNA, rRNA, tRNA, iRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., e.g., double stranded iRNAs, e.g., iRNPs). The term encompasses nucleic acids, i.e., oligonucleotides, containing known analogues of natural nucleotides. The term also encompasses nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156.

The term "Target region" or "target sequence" as used herein refers to a nucleic acid sequence that is the target of sequencing. The target sequence can be from any source such as a DNA library, genomic DNA or other source of DNA.

In one aspect, the target sequence is at least about 60 to 120 nucleic acids in length. In certain aspects the target sequence is at least about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119 or 120 nucleic acids in length.

As used herein the term "non-target sequence" refers any nucleic acid sequence that is not the target sequence. The non-target sequence may have repetitive and/or related sequences. In repetitive DNA, stretches of DNA repeats occur in the genome as either in tandem or interspersed along the genome. These sequences do not code for protein. One class termed highly repetitive DNA consists of short sequences, e.g., 5-100 nucleotides, repeated thousands of times in a single stretch and includes satellite DNA. Related sequences are sequences with high sequence identity to the target sequence but which are not identical.

As used herein "sample nucleic acid" refers to nucleic acid that contains the target sequence and non-target sequence.

The term "hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature and are well known in the art. In particular, stringency can be increased by reducing the concentration of salt, increasing the concentration of formamide, or raising the hybridization temperature. In alternative aspects, nucleic acids of the invention are defined by their ability to hybridize under various stringency conditions (e.g., high, medium, and low), as set forth herein.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS and 200 mg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The terms "capture nucleic acid molecule" or "capture bait" are used interchangeably herein and refer to nucleic acid molecules that are designed to hybridize the target sequence. Capture nucleic acid molecules are designed to specifically hybridize and isolate the target sequence.

In one aspect, the capture nucleic acid molecule has at least about 60 to 120 nucleic acids in length. In certain aspects the capture nucleic acid molecule is at least about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119 or 120 nucleic acids in length.

As used herein the terms "sequence identity" or "sequence homology," which can be used interchangeably, refer to an exact nucleotide-to-nucleotide correspondence of two polynucleotides sequences. Typically, techniques for determining sequence identity include determining the nucleotide sequence of a polynucleotide and/or determining the amino acid sequence encoded thereby, and comparing these sequences to a second nucleotide or amino acid sequence. Two or more sequences can be compared by determining their "percent identity," also referred to as "percent homology." The percent identity to a reference sequence, which may be a sequence within a longer molecule, may be calculated as the number of exact matches between two optimally aligned sequences divided by the length of the reference sequence and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul, et al., J. Mol. Biol. 215:403-410 (1990); Karlin and Altschul, Proc. Natl. Acad. Sci. USA 90:5873-5877 (1993); and Altschul et al., Nucleic Acids Res. 25:3389-3402 (1997). Briefly, the BLAST program defines identity as the number of identical aligned symbols (i.e., nucleotides or amino acids), divided by the total number of symbols in the shorter of the two sequences. The program may be used to determine percent identity over the entire length of the sequences being compared. Default parameters are provided to optimize searches with short query sequences, for example, with the blastp program. The program also allows use of an SEG filter to mask-off segments of the query sequences as determined by the SEG program of Wootton and Federhen, Computers and Chemistry 17: 149-163 (1993). Ranges of desired degrees of sequence identity are approximately 80% to 100% and integer values in between. Percent identities between a disclosed sequence and a claimed sequence can be at least 80%, at least 85%, at least 90%, at least 95%, at least 98%, at least 99%, at least 99.5%, or at least 99.9%. In general, an exact match indicates 100% identity over the length of the reference sequence. In some cases, reference to percent sequence identity refers to sequence identity as measured using BLAST (Basic Local Alignment Search Tool). In other cases, ClustalW can be used for multiple sequence alignment. Still other programs for comparing sequences and/or assessing sequence identity include the Needleman-Wunsch algorithm and the Smith-Waterman algorithm (see, e.g., the EMBOSS Water aligner. Optimal alignment may be assessed using any suitable parameters of a chosen algorithm, including default parameters.

As used herein, the term "percent (%) sequence identity" or "percent (%) identity," also including "homology," is defined as the percentage of nucleotides in a candidate sequence that are identical with the nucleotides in the reference sequences after aligning the sequences and introducing gaps, if necessary, to achieve the maximum percent sequence identity, and not considering any conservative substitutions as part of the sequence identity. Optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl. Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

In an additional aspect, the capture nucleic acid molecule has at least 70% sequence identity to the complement of the target sequence. In specific aspects, the capture nucleic acid has at least about at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to the complement of the target sequence.

In a further aspect, the capture nucleic acid molecule is labeled or tagged. Examples of nucleic acid labels include radioactive phosphates, biotin, fluorophores and enzymes. In certain aspects, the labels are used to isolate the capture nucleic acid molecules that are hybridized to the target sequence.

Methods for labeling nucleic acid are known in the art. Examples of labeling nucleic acid include DNA 5' end labeling with $\gamma$-$^{32}$P rATP; labeling by PCR with $\alpha$-$^{32}$P dNTP, Biotin-dNTP, Fl-dNTP; DNA 3' labeling with $\alpha$-$^{32}$P dNTP, Biotin-dNTP, Fl-dNTP single nucleotide terminator labeling with Fl terminator nucleotide; random priming with PCR with $\alpha$-$^{32}$P dNTP, Biotin-dNTP, Fl-dNTP; and nick translation with PCR with $\alpha$-$^{32}$P dNTP, Biotin-dNTP, Fl-dNTP.

Nucleic acid molecules can be isolated using the label or tag. For example, nucleic acid molecules labeled or tagged with biotin can be isolated using streptavidin and/or avidin. Biotin binds to streptavidin and avidin with an extremely high affinity, fast on-rate, and high specificity, and these interactions are used to isolate biotinylated molecules of interest.

The terms "blocking nucleic acid molecule" or "blocking bait" are used interchangeably and refer to nucleic acid molecules that are designed to be similar to the capture nucleic acid molecule but not identical. Blocking nucleic acid molecules are designed to hybridize to non-target sequences.

In one aspect, the blocking nucleic acid molecule is at least about 60 to 120 nucleic acids in length. In certain aspects the capture nucleic acid molecule is at least about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119 or 120 nucleic acids in length.

In an additional aspect, the blocking nucleic acid molecule has at least at least 70% sequence identity to the capture nucleic acid molecule. In specific aspects, the capture nucleic acid has at least about at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to the capture nucleic acid molecule.

In a further aspect, the blocking nucleic acid has at least about four nucleic acids different from the capture nucleic acid molecule. In specific aspects, the blocking nucleic acid molecule has at least 1, 2, 3, 4, 5, 6, 7, 8, 9, 10, 11, 12, 13, 14, 15, 16, 17, 18, 19 or 20 nucleic acids different from the capture nucleic acid molecule.

In one aspect, the blocking nucleic acid molecule is present in at least about 10 fold excess of the capture nucleic acid molecule. In certain aspects, the blocking nucleic acid molecule is present in at least about 1 fold, 2 fold, 3 fold, 4, fold, 5 fold, 6 fold, 7 fold, 8 fold, 9 fold, 10 fold, 11 fold, 12 fold, 13 fold, 14 fold, 15 fold, 16, fold, 17 fold, 18 fold, 19 fold, or 20 fold excess of the capture nucleic acid molecule.

In one aspect, the isolated target sequence is sequenced. Sequencing can be performed by any method known in the art. Exemplary sequencing methods include Next Generation Sequencing (NGS), for example. Exemplary NGS methodologies include the Roche 454 sequencer, Life Technologies SOLiD systems, the Life Technologies Ion Torrent, BGI/MGI systems, Genapsys systems, and Illumina systems such as the Illumina Genome Analyzer II, Illumina MiSeq, Illumina HiSeq, Illumina NextSeq, and Illumina NovaSeq instruments. Sequencing can be performed for deep coverage for each nucleotide, including, for example, at least 2× coverage, at least 10× coverage; at least 20× coverage; at least 30× coverage; at least 40× coverage; at least 50× coverage; at least 60× coverage; at least 70× coverage; at least 80× coverage; at least 90× coverage; at least 100× coverage; at least 200× coverage; at least 300× coverage; at least 400× coverage; at least 500× coverage; at least 600× coverage; at least 700× coverage; at least 800× coverage; at least 900× coverage; at least 1,000× coverage; at least 2,000× coverage; at least 3,000× coverage; at least 4,000× coverage; at least 5,000× coverage; at least 6,000× coverage; at least 7,000× coverage; at least 8,000× coverage; at least 9,000× coverage; at least 10,000× coverage; at least 15,000× coverage; at least 20,000× coverage; and any number or range in between.

In another embodiment, the present invention provides methods of improving sequencing specificity and/or accuracy of a target sequence by hybridizing a sample nucleic acid with a capture nucleic acid molecule and a blocking nucleic acid molecule, wherein the sample nucleic acid has the target sequence and non-target sequence; isolating the capture nucleic acid molecule hybridized to the target sequence; and sequencing the target sequence. In one aspect, the non-target sequence has a repetitive and/or related region of nucleic acid. In another aspect, the blocking nucleic acid molecule and the capture nucleic acid molecule have at least about 60 to at least about 120 nucleic acids. In an additional aspect, the capture nucleic acid is labeled with radioactive phosphates, biotin, fluorophores, enzymes or combinations thereof. In a further aspect, the blocking nucleic acid molecule is present in about 10× fold excess of the capture nucleic acid molecule. In one aspect, the blocking nucleic acid molecule has at least about 70% sequence identity to the capture nucleic acid molecule. In another aspect, the blocking nucleic acid molecule has at least about four nucleic acid molecules different from the capture nucleic acid molecule. In an additional aspect, the target sequence has at least about 60 to at least about 120 nucleic acids. In a further aspect, the sequencing is by next generation sequencing The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLES

Example 1

Identification of Blocking Baits for ROS Intron 31

Currently, it is difficult to generate high coverage of repetitive regions because of interference from related sequences. While this method will not improve selective capture of regions that are identical for longer than the bait length (often 60-120 nt), it will benefit many shorter sequences that are highly related and cause problems due to their sheer numbers rather than identity.

To identify potential blocking bait sequences, baits within capture panels that contain some of the most highly repetitive regions were examined. The primer at positions chr6: 117654887-117655006 (ROS intron 31) was analyzed using BLAT and observed to have hundreds of highly similar sequences throughout the genome. The closest 18 matches were aligned versus each other using ClustalW. There were 13 positions where the desired ROS1 intron sequence was different from the 19-sequence consensus. The mismatches were all changed to make an optimal consensus sequence for binding to the other genomic regions and reduce the likelihood of binding to ROS1. The resultant sequence was BLATted versus the genome and no perfect match was observed. All genomic sequences had at least 4 mismatches. Furthermore, the ROS1 sequence did not appear on the list of top 200 sequences. Thus, this sequence (SEQ ID NO: 1 GAACCAAAGACAAAAACCACATGATTATCTCAATA-GATGCAGAAAAGGCCTTTGAT AAAATTCAACATC CCTTCATGTTAAAAACTCTCAATAAACTAGTTATT-GATGGAACA TATCTCA) could serve as a blocking bait at >10× fold excess to prevent the undesired sequences from being captured.

Sequences used to generate consensus sequence for chr6: 117654887-117655006

TABLE 1

| QUERY | SCORE | START | END | QSIZE | IDENTITY | CHROM | STRAND | START | END | SPAN |
|---|---|---|---|---|---|---|---|---|---|---|
| 7_ros | 126 | 1 | 126 | 126 | 100.00% | chr6 | + | 117654884 | 117655009 | 126 |
| 7_ros | 108 | 1 | 125 | 126 | 90.00% | chrX | − | 116801632 | 116801750 | 119 |
| 7_ros | 106 | 1 | 125 | 126 | 89.10% | chr1 | − | 88551580 | 88551698 | 119 |
| 7_ros | 106 | 1 | 125 | 126 | 89.10% | chr5 | + | 145127454 | 145127572 | 119 |
| 7_ros | 106 | 1 | 125 | 126 | 89.80% | chr2 | + | 154220635 | 154220752 | 118 |

TABLE 1-continued

| QUERY | SCORE | START | END | QSIZE | IDENTITY | CHROM | STRAND | START | END | SPAN |
|---|---|---|---|---|---|---|---|---|---|---|
| 7_ros | 105 | 1 | 125 | 126 | 89.50% | chr22 | − | 47215292 | 47215414 | 123 |
| 7_ros | 104 | 1 | 125 | 126 | 88.30% | chr4 | + | 177836064 | 177836182 | 119 |
| 7_ros | 103 | 1 | 124 | 126 | 88.20% | chr8 | − | 79785967 | 79786084 | 118 |
| 7_ros | 103 | 1 | 125 | 126 | 87.20% | chr2 | + | 225993615 | 225993731 | 117 |
| 7_ros | 102 | 1 | 125 | 126 | 87.40% | chr3 | − | 94661910 | 94662028 | 119 |
| 7_ros | 102 | 1 | 125 | 126 | 87.40% | chr2 | − | 139864845 | 139864963 | 119 |
| 7_ros | 102 | 1 | 125 | 126 | 87.40% | chr2 | − | 22638754 | 22638872 | 119 |
| 7_ros | 102 | 1 | 125 | 126 | 89.50% | chr15 | − | 98124509 | 98124627 | 119 |
| 7_ros | 102 | 1 | 125 | 126 | 87.40% | chr1 | − | 199413444 | 199413562 | 119 |
| 7_ros | 102 | 1 | 125 | 126 | 87.40% | chr20 | + | 16915150 | 16915268 | 119 |
| 7_ros | 101 | 1 | 122 | 126 | 88.00% | chrX | − | 69145167 | 69145282 | 116 |
| 7_ros | 100 | 1 | 125 | 126 | 87.30% | chr3 | − | 118399085 | 118399203 | 119 |
| 7_ros | 100 | 1 | 125 | 126 | 87.20% | chr2 | − | 210725934 | 210725051 | 118 |

Example 2

Identification of Blocking Baits for ROS Intron 31

A second bait from ROS1 intron 31 (chr6:117654108-117654227) was examined in a similar fashion. 12 changes were made to the 120 nt bait, again resulting in a consensus sequence with no perfect matches to the genome. The top 200 matches to the consensus sequence did not include the ROS1 sequence. Thus, this consensus sequence (SEQ ID NO:2 AGAGCAAACAAATTCAAAAGCTAGCAGAAG ACAAGAAATAACTAAGATCAGAGCAGAATTGAAG-GAGATAGAGACACAAAAAACCCTCCAAAAAAAAT-CAACGAATCCAG GAGCTGTTTT) could also be used as a blocking bait.

Sequences used to generate consensus sequence for chr6: 117654108-117654227

TABLE 2

| QUERY | SCORE | START | END | QSIZE | IDENTITY | CHROM | STRAND | START | END | SPAN |
|---|---|---|---|---|---|---|---|---|---|---|
| ros3 | 120 | 1 | 120 | 120 | 100.00% | chr6 | + | 117654108 | 117654227 | 120 |
| ros3 | 97 | 1 | 114 | 120 | 90.20% | chr22 | − | 47216080 | 47216191 | 112 |
| ros3 | 97 | 1 | 120 | 120 | 92.70% | chr10 | − | 84195146 | 84195264 | 119 |
| ros3 | 97 | 1 | 120 | 120 | 90.70% | chr17 | + | 26541701 | 26541820 | 120 |
| ros3 | 96 | 1 | 120 | 120 | 88.30% | chrX | + | 43641337 | 43641455 | 119 |
| ros3 | 96 | 1 | 120 | 120 | 88.30% | chr17 | + | 51933222 | 5193340 | 119 |
| ros3 | 96 | 1 | 120 | 120 | 90.00% | chr15 | − | 61654259 | 61654378 | 120 |
| ros3 | 95 | 1 | 114 | 120 | 89.30% | chr7 | − | 10709030 | 10709141 | 112 |
| ros3 | 95 | 1 | 120 | 120 | 87.30% | chr5 | − | 34643725 | 34643842 | 118 |
| ros3 | 95 | 1 | 120 | 120 | 90.00% | chr12 | + | 23620286 | 23620405 | 120 |
| ros3 | 94 | 1 | 112 | 120 | 92.00% | chrX | − | 25354488 | 25354599 | 112 |
| ros3 | 93 | 1 | 120 | 120 | 89.80% | chr11 | + | 103784331 | 103784450 | 120 |
| ros3 | 92 | 1 | 112 | 120 | 89.90% | chr16 | − | 79888387 | 79888497 | 111 |
| ros3 | 92 | 1 | 114 | 120 | 88.50% | chr2 | − | 172614676 | 172614788 | 113 |
| ros3 | 92 | 2 | 120 | 120 | 87.90% | chr5 | − | 53147132 | 53147249 | 118 |
| ros3 | 92 | 1 | 120 | 120 | 90.40% | chr5 | − | 133669939 | 133670065 | 127 |
| ros3 | 91 | 1 | 113 | 120 | 90.30% | chr15 | + | 55076648 | 55076760 | 113 |
| ros3 | 91 | 1 | 120 | 120 | 85.00% | chr19 | + | 40213435 | 40213549 | 115 |
| ros3 | 91 | 1 | 120 | 120 | 88.30% | chr2 | − | 3860115 | 3860232 | 118 |

Applying the same methods to all regions of the targeted ROIs that have issues with related homologous sequences would provide better coverage and fewer false positives for those regions, enhancing the value of the sequencing assay. Typically, these untagged baits would be added at high molarity and those molarities could be adjusted individually or as a group to optimize performance. Individual optimization could be done empirically or using characteristics of bait sequences such as the number of mismatches, expected Tm, GC content, frequency of homologs in the genome, and/or other means.

Example 3

Identification of Blocking Baits for ROS Intron 31

Selected baits in repetitive regions of ROS1 intron 31 are shown below. The proposed sequences for the modified blocking baits are listed below each actual bait with changes in lower case or dashes. These can be used to test improvements gained through the use of blocking baits.

Table 3

| Sequence | Bed Region |
|---|---|
| CCCCAAGACACATAATCATCAGATTCTCCAAGGTTGAAATCAAGTAAAAACTGTTAAGGGCAGCCAGAGAGA AAGGCCAGGTTACCTACAAAGGGACGCCCATCAGACTAACAGTGGACC | chr6:117652685- 117652804 |
| CCCCAAGACACATAATCATCAGATTCTCCAAGGTTGAAATgAAGgAAAAAaTGTTAAGGGCAGCCAGAGAGA AAGGCCAGGTCACCTACAAAGGGAaGCCCATCAGACTAACAGTGGACC | |
| AAGCAAATGCTGAGGGATTTTGTTACCACCAGGCCTGCCCTGCAACAGCTCCTGAAATAAGCACTAAATATG GAAAGGAAAAACTGGTACCAGCCATTGCAAAAACACACCAAACTATAA | chr6:117652944- 117653063 |
| AAGCAAATGCTGAGGGATTTTGTTACCACCAGGCCTGCCtTGCAAgAGCTCCTGAAAgAAGCACTAAATATGG AAAGGAAAAACCaGTACCAGCCACTGCAAAAACACACCAAAaTATAA | |
| ACCACCAGGCCTGCCCTGCAACAGCTCCTGAAATAAGCACTAAATATGGAAAGGAAAAACTGGTACCAGCCA TTGCAAAAACACACCAAACTATAAAGATCAATGACACTATGAAGAAAC | chr6:117652968- 117653087 |
| ACCACCAGGCCTGCCtTGCAAgAGCTCCTGAAAgAAGCACTAAATATGGAAAGGAAAAACTGGTACCAGCCAc TGCAAAAACACACCAAAaTATAAAGAcCAATGACACTATGAAGAAAC | |
| CTCCTGAAATAAGCACTAAATATGGAAAGGAAAAACTGGTACCAGCCATTGCAAAAACACACCAAACTATAA AGATCAATGACACTATGAAGAAACTGCATCAACTAGCATGCAAAATAA | chr6:117652992- 117653111 |
| CTCCTGAAAgAAGCACTAAATATGGAAAGGAAAAACTGGTACCAGCCAcTGCAAAAACACACCAAAaTATAA AGAcCAATGACACTATGAAGAAACTGCATCAACTAatgTGCAAAATAA | |
| TTGCAAAAACACACCAAACTATAAAGATCAATGACACTATGAAGAAACTGCATCAACTAGCATGCAAAATAA CCAAATAGCATCATGGTGACAGGATCAAACTCACATAACAATACCTAC | chr6:117653040- 117653159 |
| cTGCAAAAACACACCAAAaTATAAAGAcCAATGACACTATGAAGAAACTGCATCAAtTAGtgTGCAAAATAACC AAATAGCATCATGaTGACAGGATCAAAtTCACAcaTAACAATACta | |
| AAAGATACAGACTGGCAAATTGGATAAGGAGTCAAGACCCATTGGTGTGTTGTATTCAGGAGATCTATCTTA CATGCAAAGACACACACAGGCTCAAAATAAAGGGATTGAGGAAAATTT | chr6:117653192- 117653311 |
| AAAGAcACAGACTGGCAAATTGGATAAaGAGTCAAGACCCATTGGTGTGcTGTATTCAGGAGAcCcATCTcAC ATGCAAAGACACACAtAGGCTCAAAATAAAGGGATgGAGGAAtATTT | |
| AGAGCAAACTAATCCAAAAGCTGGCAGAAGACAAGAAATAACTAAGATCAGAGAAGAACTGAAGGAGACA AAGACACAAAAAGCCCTCCAAAAAAAATCAACACATCCAGGAGCCGTTTT | chr6:117654108- 117654227 |
| AGAGCAAACaAATtCAAAAGCTaGCAGAAGACAAGAAATAACTAAGATCAGAGcAGAAtTGAAGGAGAtAgA GACACAAAAAaCCCTCCAAAAAAAATCAACgaATCCAGGAGCtGTTTT | |
| CCAAAGACAAAAATCACACGATTATCTGAATAGATGCAGAAAAGGCCTTTGATAAAATTCAACATCAACATCC CTTTATGTTAAAAACTCTCAATAAACTAGGTTTTTATGGAACATATC | chr6:117654887- 117655006 |
| CCAAAGACAAAAcCACAtGATTATCTcAATAGATGCAGAAAAGGCCTTTGATAAAATTCAACAT------ CCCTTcATGTTAAAAACTCTCAATAAACTAGGTaTTgATGGAACATATC | |
| GCCCAGCATGCATTAGCTATTTTTCCTAATACTCTCTATCCCCCCACCCCTCCCCCTGACAGGCCCCAGTGTGT GTTGTTCCCCTCCTTGTGTCCATGCGTTCTCATTGTFCAGCTCCCA | chr6:117657443- 117657562 |
| GCCCAGCATGCATTAGCTATTTTTCCTAATgCTCTCccTCCCCCaACCCCTCCCCCcaACAGGCCCCAGTGTGTGT TGTTCCCCTCCcTGTGTCCATGtGTTCTCATTGTTCAGCTCCCA | |
| CCTCCCCCTGACAGGCCCCAGTGTGTGTTGTTCCCCTCCTTGTGTCCATGCGTTCTCATTGTTCAGCTCCCACTT GTAAGTGAGAACACGCAGTGTTTGGTTTTCTGTTCCTGAATTAGT | chr6:117657491- 117657610 |
| CCcaCCCCTGACAGGCCCCAGTGTGTGTTGTTCCCCTCCCTGTGTCCATGGTTCTCATTGTTCAGCTCCCACTTa TAAGTGAGAACAtGCAGTGTTTGGTTTTCTGTTCCTGCATTAGT | |
| GTGTTGTTCCCCTCCTTGTGTCCATGCGTTCTCATTGTTCAGCTCCCACTTGTAAGTGAGAACACGCAGTGTTT GGTTTTCTGTTCCTGAATTAGTTTGCTGAGGTTAATAGCTTCCAGC | chr6:117657515- 117657634 |
| GTGTTGTTCCCCTCCcTGTGTCCATGtGTTCTCATTGTTCAGCTCCCACTTaTAAGTGAGAACAGTGTTTGGTTT TCTGTTCCTGtgTTAGTTTGCTGAGGaTAATgGCTTCCAGC | |
| TGCGTTCTCATTGTTCAGCTCCCACTTGTAAGTGAGAACACGCAGTGTTTGGTTTTCTGTTCCTGAATTAGTTT GCTGAGGTTAATAGCTTCCAGCTTCATCCATATCCCTGCAAAAAA | chr6:117657539- 117657658 |
| TGtGTTCTCATTGTTCAGCTCCCACTTaTAAGTGAGAACAtGCAGTGTTTGGTTTTCTGTTCCTGcgTTAGTTTGC TGAGGTTAATgGCTTCCAGCTcCATCCATgTCCCTGCAAAgcac | |

Although the invention has been described with reference to the above examples, it will be understood that modifications and variations are encompassed within the spirit and scope of the invention. Accordingly, the invention is limited only by the following claims.

What is claimed is:

1. A method of sequencing a target sequence comprising:
    a) hybridizing a sample nucleic acid with a capture nucleic acid molecule and a blocking nucleic acid molecule, wherein the sample nucleic acid comprises the target sequence and non-target sequence, wherein the blocking nucleic acid molecule is identified using BLAST-like alignment tool (BLAT) and wherein the blocking nucleic acid molecule has at least about 70% sequence identity to the capture nucleic acid molecule and has at least about four nucleic acid molecules different from the capture nucleic acid molecule
    b) isolating the capture nucleic acid molecule hybridized to the target sequence; and
    c) sequencing the isolated target sequence.

2. The method of claim 1, wherein the non-target sequence comprises a repetitive and/or related region of nucleic acid.

3. The method of claim 1, wherein the blocking nucleic acid molecule and the capture nucleic acid molecule comprise at least 60 to 120 nucleic acids.

4. The method of claim 1, wherein the capture nucleic acid is labeled.

5. The method of claim 4, wherein the capture nucleic acid is labeled with a label selected from the group consisting of radioactive phosphates, biotin, fluorophores, enzymes or combinations thereof.

6. The method of claim 1, wherein the blocking nucleic acid molecule is present in 10× fold excess of the capture nucleic acid molecule.

7. The method of claim 1, wherein the target sequence comprises at least 60 to 120 nucleic acids.

8. The method of claim 1, wherein the sequencing comprises next generation sequencing.

9. A method of improving sequencing specificity and/or accuracy of a target sequence comprising:
 a) hybridizing a sample nucleic acid with a capture nucleic acid molecule and a blocking nucleic acid molecule wherein the sample nucleic acid comprises the target sequence and non-target sequence, wherein the blocking nucleic acid molecule is identified using BLAST-like alignment tool (BLAT) and wherein the blocking nucleic acid molecule has at least about 70% sequence identity to the capture nucleic acid molecule and has at least about four nucleic acid molecules different from the capture nucleic acid molecule;
 b) isolating the capture nucleic acid molecule hybridized to the target sequence; and
 c) sequencing the target sequence.

10. The method of claim 9, wherein the non-target sequence comprises a repetitive and/or related region of nucleic acid.

11. The method of claim 9, wherein the blocking nucleic acid molecule and the capture nucleic acid molecule comprise at least about 60 to 120 nucleic acids.

12. The method of claim 9, wherein the capture nucleic acid is labeled.

13. The method of claim 12, wherein the capture nucleic acid is labeled with a label selected from the group consisting of radioactive phosphates, biotin, fluorophores, enzymes or combinations thereof.

14. The method of claim 9, wherein the blocking nucleic acid molecule is present in 10× fold excess of the capture nucleic acid molecule.

15. The method of claim 9, wherein the target sequence comprises at least 60 to 120 nucleic acids.

16. The method of claim 9, wherein the sequencing comprises next generation sequencing.

17. The method of claim 1 or 9, wherein the blocking nucleic acid molecule is identified using BLAST-like alignment tool (BLAT) with primers that bind to the target sequence.

18. The method of claim 17, wherein sequences identified from BLAT are aligned to provide optimal consensus sequences for binding to genomic regions other than the target sequence.

19. The method of claim 18, wherein the alignment is performed using a multiple sequence alignment program.

20. The method of claim 19, wherein the alignment program is ClustalW.

* * * * *

```
                              SEQUENCE LISTING

<160> NUMBER OF SEQ ID NOS: 25

<210> SEQ ID NO 1
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gaaccaaaga caaaaaccac atgattatct caatagatgc agaaaaggcc tttgataaaa      60
ttcaacatcc cttcatgtta aaaactctca ataaactagt tattgatgga acatatctca    120

<210> SEQ ID NO 2
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
agagcaaaca aattcaaaag ctagcagaag acaagaaata actaagatca gagcagaatt      60
gaaggagata gagacacaaa aaaccctcca aaaaaaatca acgaatccag gagctgtttt    120

<210> SEQ ID NO 3
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
ccccaagaca cataatcatc agattctcca aggttgaaat caagtaaaaa ctgttaaggg      60
cagccagaga gaaaggccag gttacctaca aagggacgcc catcagacta acagtggacc    120

<210> SEQ ID NO 4
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
ccccaagaca cataatcatc agattctcca aggttgaaat gaaggaaaaa atgttaaggg      60
cagccagaga gaaaggccag gtcacctaca aagggaagcc catcagacta acagtggacc    120

<210> SEQ ID NO 5
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
```
aagcaaatgc tgagggattt tgttaccacc aggcctgccc tgcaacagct cctgaaataa    60
gcactaaata tggaaaggaa aaactggtac cagccattgc aaaaacacac caaactataa    120

<210> SEQ ID NO 6
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
aagcaaatgc tgagggattt tgttaccacc aggcctgcct tgcaagagct cctgaaagaa    60
gcactaaata tggaaaggaa aaaccagtac cagccactgc aaaaacacac caaaatataa    120

<210> SEQ ID NO 7
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
accaccaggc ctgccctgca acagctcctg aaataagcac taaatatgga aaggaaaaac    60
tggtaccagc cattgcaaaa acacaccaaa ctataaagat caatgacact atgaagaaac    120

<210> SEQ ID NO 8
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
accaccaggc ctgccttgca agagctcctg aaagaagcac taaatatgga aggaaaaac    60 tggtaccagc cactgcaaaa acacaccaaa atataaagac caatgacact atgaagaaac    120

<210> SEQ ID NO 9
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
ctcctgaaat aagcactaaa tatggaaagg aaaaactggt accagccatt gcaaaaacac    60
accaaactat aaagatcaat gacactatga agaaactgca tcaactagca tgcaaaataa    120

<210> SEQ ID NO 10
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
ctcctgaaag aagcactaaa tatggaaagg aaaaactggt accagccact gcaaaaacac    60
accaaaatat aaagaccaat gacactatga agaaactgca tcaactaatg tgcaaaataa    120

<210> SEQ ID NO 11
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
ttgcaaaaac acaccaaact ataaagatca atgacactat gaagaaactg catcaactag     60
catgcaaaat aaccaaatag catcatggtg acaggatcaa actcacataa caatacctac    120

<210> SEQ ID NO 12
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
ctgcaaaaac acaccaaaat ataaagacca atgacactat gaagaaactg catcaattag     60
tgtgcaaaat aaccaaatag catcatgatg acaggatcaa attcacacat aacaatacta    120

<210> SEQ ID NO 13
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
aaagatacag actggcaaat tggataagga gtcaagaccc attggtgtgt tgtattcagg     60
agatctatct tacatgcaaa gacacacaca ggctcaaaat aaagggattg aggaaaattt    120

<210> SEQ ID NO 14
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
aaagacacag actggcaaat tggataaaga gtcaagaccc attggtgtgc tgtattcagg     60
agacccatct cacatgcaaa gacacacata ggctcaaaat aaagggatgg aggaatattt    120

<210> SEQ ID NO 15
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15 agagcaaaact aatccaaaag ctggcagaag acaagaaata actaagatca gagaagaact    60
gaaggagaca aagacacaaa aagccctcca aaaaaaatca acacatccag gagccgtttt    120

<210> SEQ ID NO 16
<211> LENGTH: 120

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
ccaaagacaa aaatcacacg attatctgaa tagatgcaga aaaggccttt gataaaattc    60
aacatcaaca tcccttatg ttaaaaactc tcaataaact aggtttttat ggaacatatc   120

<210> SEQ ID NO 17
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
ccaaagacaa aaccacatg attatctcaa tagatgcaga aaaggccttt gataaaattc    60
aacatccctt catgttaaaa actctcaata aactaggtat tgatggaaca tatc        114

<210> SEQ ID NO 18
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gcccagcatg cattagctat ttttcctaat actctctatc ccccacccc tcccctgac     60 aggccccagt gtgtgttgtt ccctccttg tgtccatgcg ttctcattgt tcagctccca  120

<210> SEQ ID NO 19
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
gcccagcatg cattagctat ttttcctaat gctctccctc cccaaccccc tcccccaac    60 aggccccagt gtgtgttgtt ccctcccctg tgtccatgtg ttctcattgt tcagctccca  120

<210> SEQ ID NO 20
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20 cctcccctg acaggcccca gtgtgtgttg ttcccctcct tgtgtccatg cgttctcatt    60
gttcagctcc cacttgtaag tgagaacacg cagtgtttgg ttttctgttc ctgaattagt  120

<210> SEQ ID NO 21
<211> LENGTH: 120
<212> TYPE: DNA
<213> ORGANISM: Artificial Sequence
<220> FEATURE:
<223> OTHER INFORMATION: Description of Artificial Sequence: Synthetic
```

-continued polynucleotide

<400> SEQUENCE: 21
cccacccctg acaggcccca gtgtgtgttg ttcccctccc tgtgtccatg tgttctcatt    60
gttcagctcc cacttataag tgagaacatg cagtgtttgg ttttctgttc ctgcattagt   120

<210> SEQ ID NO 22
<211> LENGTH: 120
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 22
gtgttgttcc cctccttgtg tccatgcgtt ctcattgttc agctcccact tgtaagtgag    60
aacacgcagt gtttggtttt ctgttcctga attagtttgc tgaggttaat agcttccagc   120

<210> SEQ ID NO 23
<211> LENGTH: 120
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 23
gtgttgttcc cctccctgtg tccatgtgtt ctcattgttc agctcccact tataagtgag    60
aacatgcagt gtttggtttt ctgttcctgt gttagtttgc tgaggataat ggcttccagc   120

<210> SEQ ID NO 24
<211> LENGTH: 120
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 24
tgcgttctca ttgttcagct cccacttgta agtgagaaca cgcagtgttt ggttttctgt    60
tcctgaatta gtttgctgag gttaatagct tccagcttca tccatatccc tgcaaaaaaa   120

<210> SEQ ID NO 25
<211> LENGTH: 120
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 25
tgtgttctca ttgttcagct cccacttata agtgagaaca tgcagtgttt ggttttctgt    60
tcctgcgtta gtttgctgag gttaatggct tccagctcca tccatgtccc tgcaaagcac   120